(12) United States Patent
Chang et al.

(10) Patent No.: US 10,325,676 B2
(45) Date of Patent: Jun. 18, 2019

(54) METHOD AND SYSTEM FOR HIGH-THROUGHPUT SEQUENCING DATA ANALYSIS

(71) Applicant: Atgenomix Inc., Taipei (TW)

(72) Inventors: Ming-Tai Chang, New Taipei (TW); Chung-Tsai Su, New Taipei (TW); Yun-Chian Cheng, Merced, CA (US)

(73) Assignee: ATGENOMIX INC., Taipei (TW)

( * ) Notice: Subject to any disclaimer, the term of this patent is extended or adjusted under 35 U.S.C. 154(b) by 648 days.

(21) Appl. No.: 14/985,758

(22) Filed: Dec. 31, 2015

(65) Prior Publication Data

US 2016/0188797 A1 Jun. 30, 2016

Related U.S. Application Data

(60) Provisional application No. 62/230,741, filed on Jun. 15, 2015.

(51) Int. Cl.
*G16B 50/00* (2019.01)
*G06F 16/22* (2019.01)
*G16B 30/00* (2019.01)

(52) U.S. Cl.
CPC .......... *G16B 50/00* (2019.02); *G06F 16/2255* (2019.01); *G06F 16/2282* (2019.01); *G16B 30/00* (2019.02)

(58) Field of Classification Search
None
See application file for complete search history.

(56) References Cited

U.S. PATENT DOCUMENTS 4,771,384 A 9/1988 Daniels et al.
9,109,861 B1 8/2015 Blattner et al.
2013/0184161 A1 7/2013 Kingsmore et al.
2014/0032579 A1* 1/2014 Merriman ......... G06F 17/30345
 707/756
2014/0051154 A1 2/2014 Hyland et al.

OTHER PUBLICATIONS

Fei Nan, 2008. Direct Suffix Sorting and Its Application. 2008.*
Nguyen et al. BMC Research Notes. 2011. CloudAligner: A fast and full-featured MapReduce Based Tool for Sequence Mapping (Year: 2011).*

* cited by examiner

*Primary Examiner* — Tuankhanh D Phan
(74) *Attorney, Agent, or Firm* — WPAT, PC

(57) ABSTRACT

Methods and systems for high-throughput sequencing data analysis are provided. In an embodiment, the method includes the following steps. An input DNA/RNA/Protein sequence is received by a master computing unit. The input DNA/RNA/Protein sequence is partitioned into overlapping segments with a sliding window less than a segment length of the overlapping segments to allow overlapping of any successive two thereof by the master computing unit. The overlapping segments are distributed by the master computing unit to a plurality of slave computing units in a cloud computing environment. Suffix-expansion-sorting processing is performed on the overlapping segments by the slave computing units to produce sorted expansion segments. Distributed database tables are generated based on the sorted expansion segments by at least a portion of the slave computing units. The distributed database tables are associated to construct a global database table corresponding to the input DNA/RNA/Protein sequence for high-throughput sequencing data analysis.

12 Claims, 15 Drawing Sheets

Specification includes a Sequence Listing.

SEQUENCE LISTING

<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: The sequence is synthesized

<400> SEQUENCE: 1
atcgaattcc gg                                                                  12

<210> SEQ ID NO 2
<211> LENGTH: 12
<212> TYPE: DNA
<213> ORGANISM: Artificial Sequence
<220> FEATURE:
<223> OTHER INFORMATION: The sequence is synthesized

<400> SEQUENCE: 2
gctaaattcc gg                                                                  12

<210> SEQ ID NO 3
<211> LENGTH: 11
<212> TYPE: DNA
<213> ORGANISM: Artificial Sequence
<220> FEATURE:
<223> OTHER INFORMATION: The sequence is synthesized

<400> SEQUENCE: 3
tcgaattccg g                                                                   11

<210> SEQ ID NO 4
<211> LENGTH: 10
<212> TYPE: DNA
<213> ORGANISM: Artificial Sequence
<220> FEATURE:
<223> OTHER INFORMATION: The sequence is synthesized

<400> SEQUENCE: 4
cgaattccgg                                                                     10

<210> SEQ ID NO 5
<211> LENGTH: 11
<212> TYPE: DNA
<213> ORGANISM: Artificial Sequence
<220> FEATURE:
<223> OTHER INFORMATION: The sequence is synthesized

<400> SEQUENCE: 5
ctaaattccg g                                                                   11

<210> SEQ ID NO 6
<211> LENGTH: 10
<212> TYPE: DNA
<213> ORGANISM: Artificial Sequence
<220> FEATURE:
<223> OTHER INFORMATION: The sequence is synthesized

<400> SEQUENCE: 6
taaattccgg                                                                     10

METHOD AND SYSTEM FOR HIGH-THROUGHPUT SEQUENCING DATA ANALYSIS

CROSS-REFERENCES TO RELATED APPLICATION

This non-provisional application claims priority under 35 U.S.C. § 119(a) on Provisional Patent Application No. 62/230,741 filed on Jun. 15, 2015, the entire contents of which are hereby incorporated by reference.

BACKGROUND

Technical Field

The present invention relates to methods and systems for high-throughput sequencing data analysis.

Related Art

INCORPORATION OF SEQUENCE LISTING

The entire contents of a copy of the "Sequence Listing" in computer readable form (.txt) that is identical to the PatentIn 3.5 computer software generated sequence listing containing the file named 14985758_Sequence_Listing_ST25.txt, which is 2 kilobytes in size and was created on Jan. 26, 2016, is herein incorporated by reference in its entirety.

Current technologies are based on either single processing unit limited by system memory/disk size or pre-partitioning the data corpus into smaller subset and each is stored in a separate processing unit, which is only limited to analyze a small portion of the data and is not able to obtain the global insights across all the data points.

For the foregoing reasons, there is a need for systems and methods for effectively providing sequencing data analysis.

SUMMARY

Millions of genomic sequencing data are generated each day, e.g., human whole genome sequences and whole exome sequences; in order to understand the broader insights ones need to have an efficient and effective way to process and analyze from the large cohort of those data. Accordingly, the invention provides methods and systems for high-throughput sequencing data analysis in various embodiments. Based on this invention, the similarity and variation among a very large portion of sequencing data can be searched rapidly and identified accurately. Some embodiments of the invention also inherit the scalability by the nature of big data technology as the data grows. In the following, various embodiments for use in bioinformatics applications will be provided according to the invention.

According to an embodiment of the invention, a method for high-throughput sequencing data analysis is provided. The method comprises the following steps. An input DNA/RNA/Protein sequence is received by a master computing unit. The input DNA/RNA/Protein sequence is partitioned into a plurality of overlapping segments with a sliding window less than a segment length of the overlapping segments to allow overlapping of any successive two of the overlapping segments by the master computing unit. The plurality of overlapping segments are distributed by the master computing unit to a plurality of slave computing units in a cloud computing environment. Suffix-expansion-sorting processing is performed on the overlapping segments by the slave computing units to produce a plurality of sorted expansion segments. A plurality of distributed database tables are generated based on the sorted expansion segments by at least a portion of the slave computing units. The distributed database tables generated by the slave computing units are associated to construct a global database table corresponding to the input DNA/RNA/Protein sequence for high-throughput sequencing data analysis.

According to another embodiment of the invention, a method for high-throughput sequencing data analysis is provided. The method comprises the following steps. An input DNA/RNA/Protein sequence is received by a master computing unit. The input DNA/RNA/Protein sequence is partitioned into a plurality of overlapping segments with a sliding window less than a segment length of the overlapping segments to allow overlapping of any successive two of the overlapping segments by the master computing unit. Suffix-expansion processing is performed on the overlapping segments by the master computing unit to produce a plurality of suffix expansion segments. The plurality of suffix expansion segments are distributed, by the master computing unit, to a plurality of slave computing units in a cloud computing environment. Sorting processing is performed on the suffix expansion segments by the slave computing units to produce a plurality of sorted expansion segments. A plurality of distributed database tables are generated based on the sorted expansion segments by at least a portion of the slave computing units. The distributed database tables generated by the slave computing units are associated to construct a global database table corresponding to the input DNA/RNA/Protein sequence for high-throughput sequencing data analysis.

According to another embodiment of the invention, a system for high-throughput sequencing data analysis which includes a master computer unit and a plurality of slave computing units. The master computing unit comprises a processing device and a networking device. The slave computing units are communicatively coupled to the master computing unit in a cloud computing environment, wherein each of the slave computing units comprising a processing device and a networking device. The system can implement each of the embodiments above.

For better understanding of the above and other aspects of the invention, a plurality of embodiments or examples will be taken with accompanying drawings to provide detailed description as follows.

DETAILED DESCRIPTION

Figure 1:
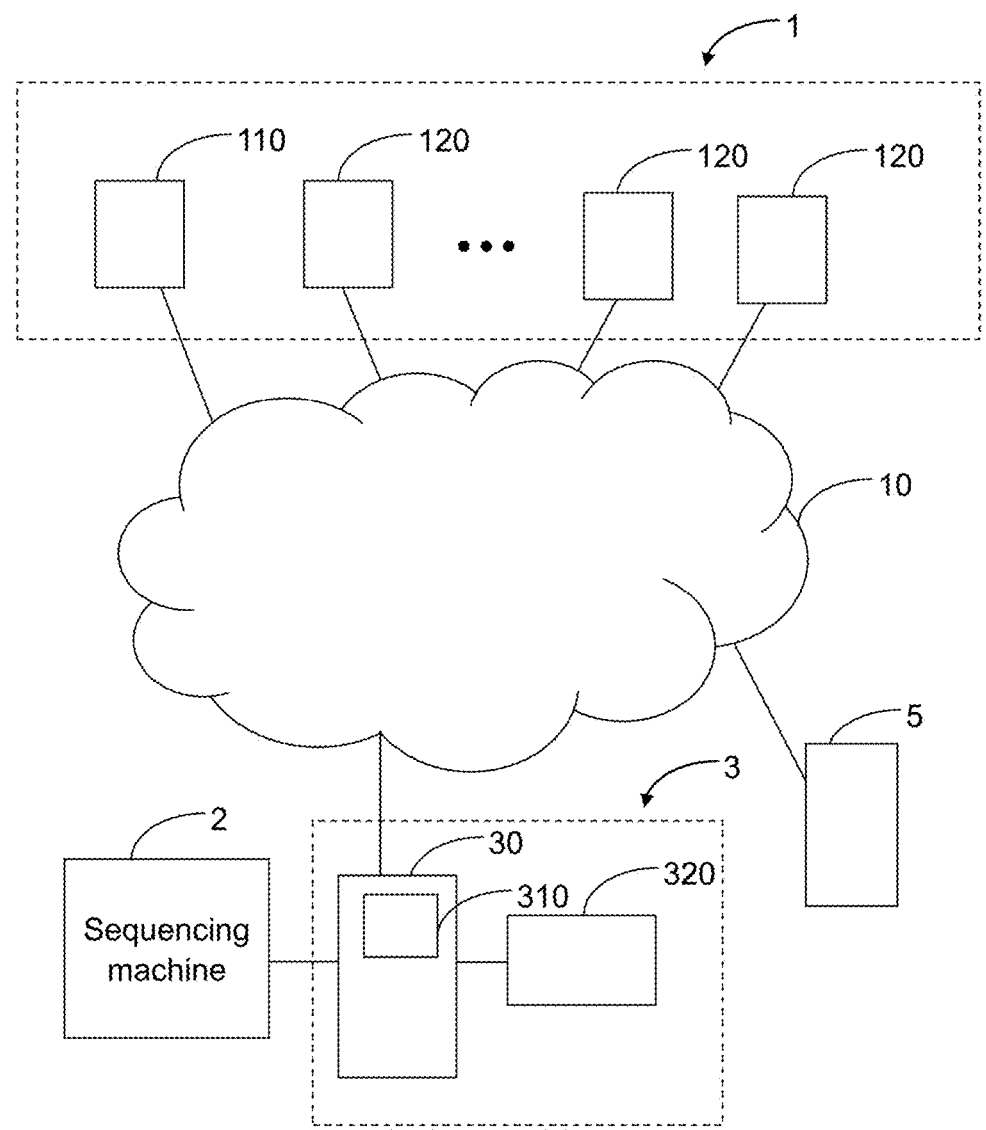
FIG. 1 is a block diagram illustrating a system for high-throughput sequencing data analysis, according to various embodiments.

Embodiments of systems and methods for high-throughput sequencing data analysis are described herein. According to the present teachings, high-throughput sequencing data analysis can be achieved for DNA or RNA or protein sequencing by way of construction of a global database table over a distributed or cloud computing environment, thus facilitating other applications or operations such as query, incremental construction of the table, and so on. Further, the invention may be utilized in large cohort of sequential data processing and pattern mining in the various domain applications, such as population-based genomic analysis in bioinformatics, user behavior analysis in web clickstreams and social networks, anomaly detection in network security events, and so on.

In this detailed description of the various embodiments, for purposes of explanation, numerous specific details are set forth to provide a thorough understanding of the embodiments disclosed. One skilled in the art will appreciate, however, that these various embodiments may be implemented with or without these specific details. In other instances, structures and devices are shown in block diagram form. Furthermore, one skilled in the art can readily appreciate that the specific orders in which methods are presented and performed are illustrative and it is contemplated that the orders can be varied and still remain within the spirit and scope of the various embodiments disclosed herein.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization.

It is well known that DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. It is also known that certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

FIG. 1 is a block diagram illustrating a high-throughput sequencing data analysis system, according to various embodiments. As shown in FIG. 1, a high-throughput sequencing data analysis system 1, a sequencing machine 2, and an analytic computing unit 3 are presented. For a given sample, the sequencing machine 2 outputs a plurality of sequence "reads", sequence data, in terms of a list of bases. The analytic computing unit 3 is configured to receive and perform data processing on the sequence data for further sequencing analysis by way of bioinformatics techniques, for example, by executing one or more application programs using one or more processing units 310; the analysis output can be further presented on a display device 320 visually by graphical interfaces or schematic diagrams, or statistically by charts or bars, or in terms of indications of the bases in string form. In addition, the analytic computing unit 3 can communicate with the high-throughput sequencing data analysis system 1 via a communication network 10 in order to perform high-throughput sequencing data analysis by a plurality of computing units (such as computing units (110, 120)) in a distributed or cloud computing environment. In an embodiment, the high-throughput sequencing data analysis system 1 can construct a global database table for an input sequence by a plurality of computing units so that the subsequent operations, such as query, or incremental construction of the global database table, can be performed effectively.

Referring to FIG. 1, at least one sequencing machine 2, such as a Next Generation Sequencers (NGS), a third generation DNA sequencer, a nucleic acid sequencer, a polymerase chain reaction (PCR) machine, or a protein sequencing machine, is used to automate the DNA or RNA or protein (DNA/RNA/protein) sequencing process. In an example of DNA sequencing, given a sample of DNA, a sequencing machine 2 for DNA sequencing is used to determine the order of the four bases: G (guanine), C (cytosine), A (adenine) and T (thymine) for the sample. This order of the bases is then reported by the sequencing machine 2 as a text string, called a read. In an example for RNA sequencing, given a sample of RNA, a sequencing machine 2 for RNA sequencing is used to determine the order of the four bases: A, U (uracil), G, and C for the sample. In another example for protein sequencing, given a sample of protein, a sequencing machine 2 for protein sequencing is used to determine the order of at least 20 bases (i.e., amino acids) for the sample. For example, the sequencing machine 2 can be configured to sequence a plurality of nucleic acid fragments obtained from a single biological sample and generate a data file containing a plurality of fragment sequence reads that are representative of the genomic profile of the biological sample.

In another embodiment, a client terminal 5 can be linked to the high-throughput sequencing data analysis system 1 to request for sequencing analysis by uploading sequencing data files or making query for sequence analysis, and so on. The client terminal 5 can be a thin client or thick client computing device. In various embodiments, client terminal 5 can have a web browser (e.g., CHROME, INTERNET EXPLORER, FIREFOX, SAFARI, etc) or an application program that can be used to request the high-throughput sequencing data analysis system 1 for the analytic operations. For example, the client terminal 5 can be used to configure the operating parameters (e.g., mismatch constraint, quality value thresholds, window region sizing parameters, etc.) for sequencing data analysis, depending on the requirements of a particular application or implementation of the high-throughput sequencing data analysis system 1. The client terminal 5 can also display the results of the analysis performed. In various embodiments, the analytics computing unit 3 or client terminal 5 can be a workstation, mainframe computer, personal computer, mobile device, etc.

I. Construction of Global Database Table

Figure 2:
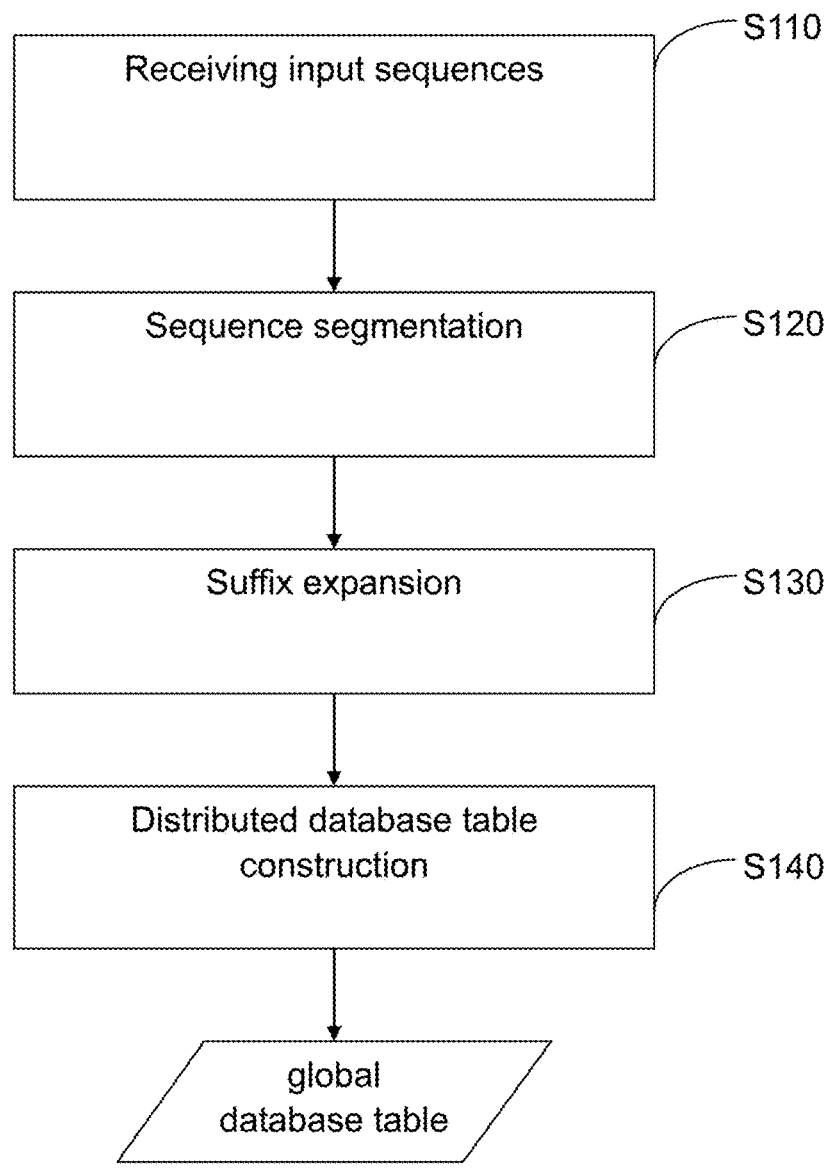
FIG. 2 is a flowchart showing a method for high-throughput sequencing data analysis, related to construction of a global database table, according to an embodiment.

FIG. 2 is a flowchart showing a method for high-throughput sequencing data analysis, related to construction of a global database table, according to an embodiment. As shown in FIG. 2, in step S110, input sequence(s) is received. In step S120, sequence segmentation is performed on the input sequence. In step S130, suffix expansion is performed on the outputs of the sequence segmentation. In step S140, a plurality of distributed database table is constructed based on the outputs of the suffix expansion.

For example, the method in FIG. 2 can be implemented to split the input sequences and store all the valid suffixes of the given input sequences in a big table implementation as a large distributed suffix array, where each suffix represents a row key. The design of the row key has the common prefix of the input suffix along with the remaining suffix, where the common prefix can be applied with a hashing mechanism in order to avoid hotspot and keep the prefix short with fixed length for better search performance in big table.

In an example, the global database table is a suffix-based big table (SBT). In this example, the input sequences are distributed to a plurality of computing units in step S110. In step S120, a sequence is partitioned into smaller segments with a sliding window less than a segment length to allow overlapping of successive segments. In step S130, for a given subset of segments in each computing unit, all suffixes of the segments are expanded and sorted; from the list of sorted suffixes, all the common prefixes with a length >=N (in a trivial case, N is 1) along with which the corresponding remaining suffix are outputted. In step S140, for each output from step S130, a row key is constructed by appending a hash value of the common prefix with the remaining suffix, and is inserted into the suffix big table (SBT) provided by the plurality of computing units, and the entire common prefix is stored as a column value along with other values as required by a given application. In step S130, data shuffling between the computing units can be performed, and the common prefixes can be sorted by length and alphabetically.

In addition, sequence suffixes are the key data elements in computational pattern matching, which allows various sophisticated operations to be performed efficiently, such as suffix tree and suffix array. By leveraging the characteristics and functions of the sequence suffix structures, some embodiments of the invention present a novel and efficient computer-implemented method for finding sequence patterns, the longest repeated subsequences, the longest common subsequences, tandem repeats with mismatches, and etc. in a generalized suffix-based big table, such as Apache HBase, HyperTable, MapR-DB, and so on, which represents all the suffixes of large N sequence set.

In some embodiments, the above-mentioned data shuffling between the computing units can be implemented based on any distributed processing model for large-scale data-intensive applications, such as "MapReduce." The MapReduce framework can simplify the complexity of running distributed data processing functions across multiple computing nodes in a cluster. The embodiments involve data shuffling will be provided later.

By the above example, entire or a portion of a reference sequence (e.g., DNA sequence) can be represented by way of the global database table which can be a suffix-based big table (SBT) and regarded as a tree (e.g., a data structure representation). Further operations for high-throughput sequencing data analysis can then be implemented optionally, as exemplified as in FIGS. 3 and 4.

Figure 3:
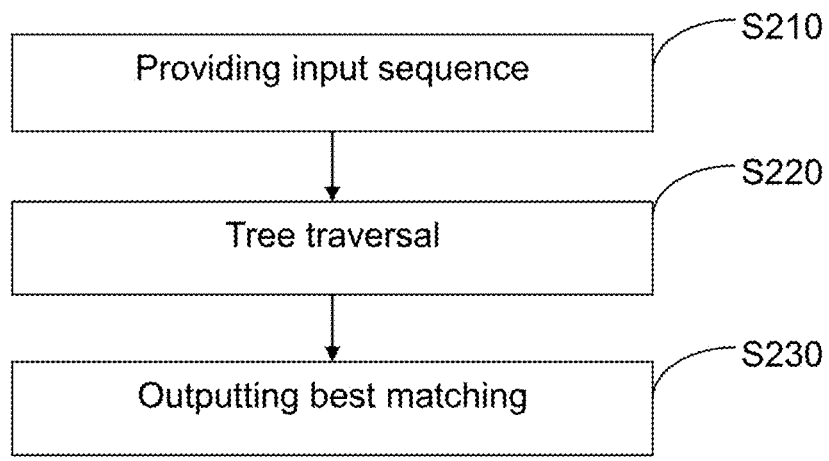
FIG. 3 is a flowchart showing a method for high-throughput sequencing data analysis, related to query on the global database table, according to an embodiment.

FIG. 3 is a flowchart showing a method for high-throughput sequencing data analysis, related to query on the global database table, according to an embodiment. As shown in FIG. 3, in step S210, an input sequence is provided, such as one or more soft-clipping sequences. In step S220, tree traversal is performed with respect to the input sequence, by way of a plurality of computing units. In step S230, a best matching is outputted.

Figure 4:
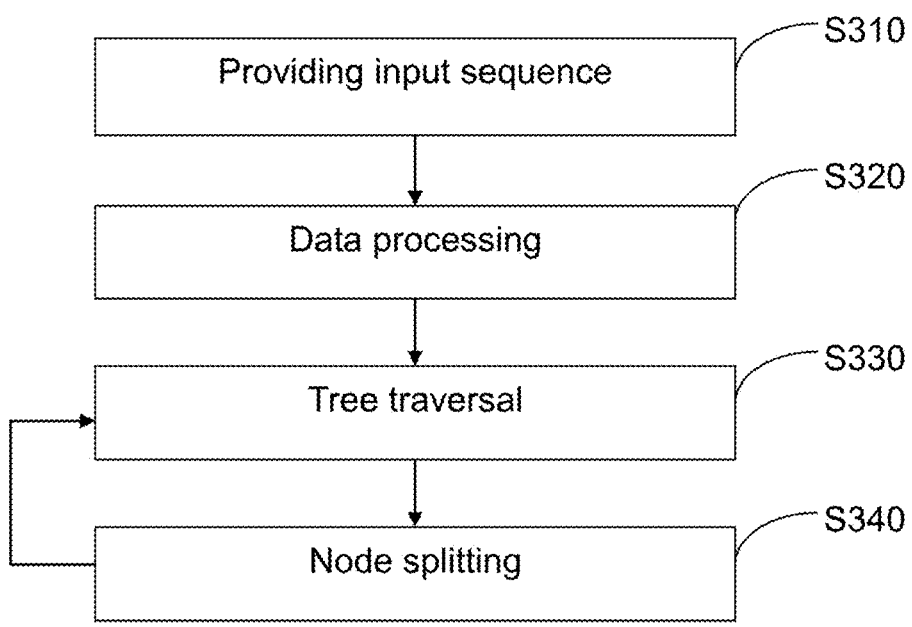
FIG. 4 is a flowchart showing a method for high-throughput sequencing data analysis, related to incremental construction based on the global database table, according to an embodiment.

FIG. 4 is a flowchart showing a method for high-throughput sequencing data analysis, related to incremental construction based on the global database table, according to an embodiment. As shown in FIG. 4, in step S310, an input sequence is provided, for example, a DNA sequence from a patient as a new reference. In step S320, data processing (such as step S120, S130) is performed with respect to the input sequence, by way of a plurality of computing units. In step S330, tree traversal is performed with respect to the input sequence, by way of the computing units. In step S340, node splitting is performed based on a node found by the tree traversal of step S330. Steps S330 and S340 can be repeated also for incrementally inserting a number of new sequences into the tree indicated by the global database table.

In the following, methods for high-throughput sequencing data analysis, related to construction of a global database table, according to various embodiments are further provided.

Figure 6:
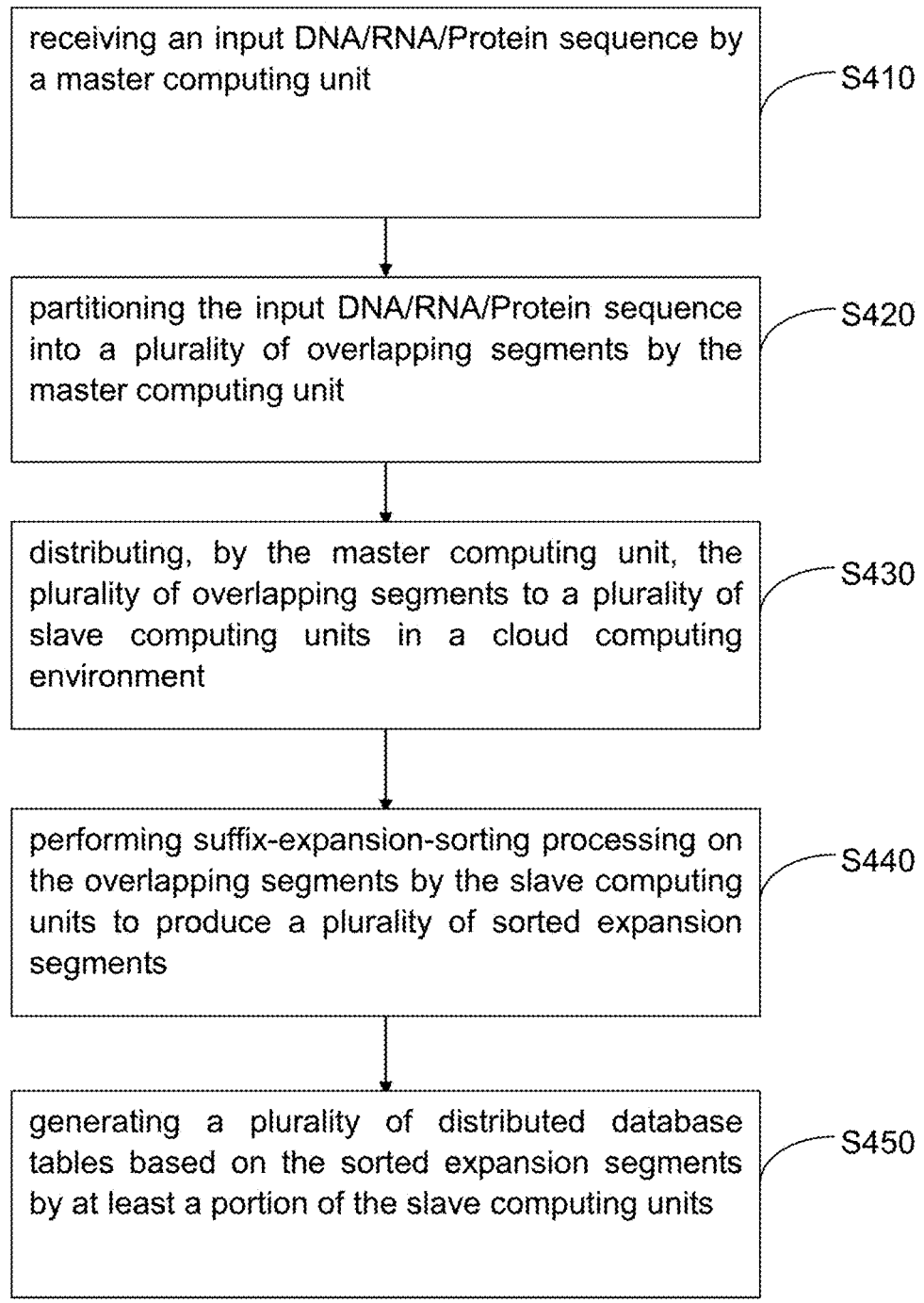
FIG. 6 is a flowchart showing a method for high-throughput sequencing data analysis, related to construction of a global database table, according to an embodiment.

FIG. 6 is a flowchart showing a method for high-throughput sequencing data analysis, related to construction of a global database table, according to an embodiment. As shown in FIG. 6, the method for high-throughput sequencing data analysis includes the following. In step S410, an input DNA/RNA/Protein sequence is received by a master computing unit, such as the computing unit 110 as illustrated in FIG. 1. In step S420, the input DNA/RNA/Protein sequence is partitioned into a plurality of overlapping segments with a sliding window less than a segment length of the overlapping segments to allow overlapping of any successive two of the overlapping segments by the master computing unit. In step S430, the plurality of overlapping segments are distributed by the master computing unit to a plurality of slave computing units, such as the computing units 120 as illustrated in FIG. 1, in a cloud computing environment. In step S440, suffix-expansion-sorting processing is performed on the overlapping segments by the slave computing units to produce a plurality of sorted expansion segments. In step S450, a plurality of distributed database tables are generated based on the sorted expansion segments by at least a portion of the slave computing units. The distributed database tables generated by the slave computing units are associated to construct a global database table corresponding to the input DNA/RNA/Protein sequence for high-throughput sequencing data analysis.

Figure 5:
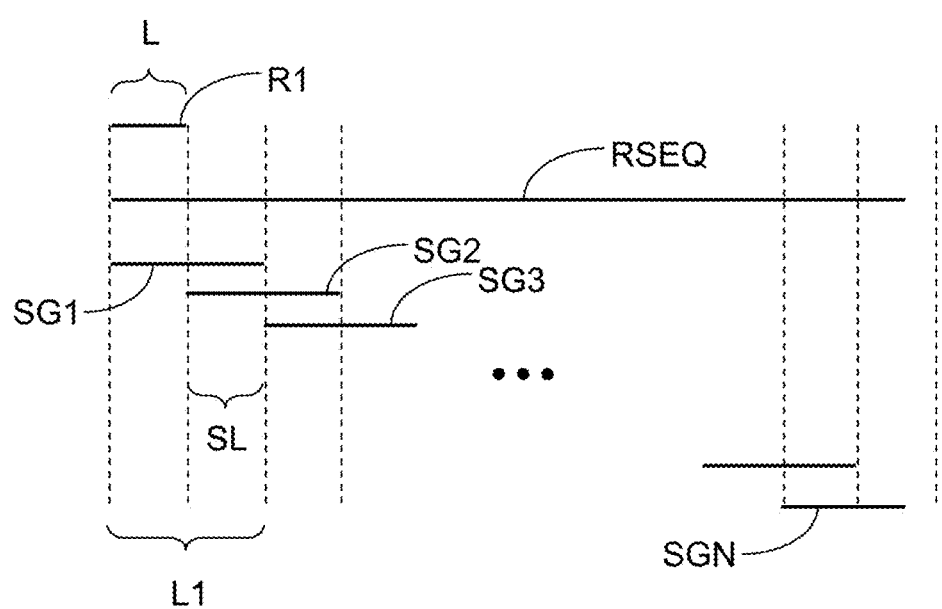
FIG. 5 is a schematic diagram illustrating sequence segmentation, according to various embodiments.

For example, sequence segmentation, as in step S410, is illustrated in a schematic diagram of FIG. 5, according to various embodiments. As illustrated in FIG. 5, a reference sequence is represented by a line segment, denoted by RSEQ, which may indicate a DNA or RNA sequence of a number of gigabytes; and the reference sequence is fragmented into a plurality of overlapping segments (denoted by SG1, SG2, SG3, . . . , SGN). The overlapping segments, SG1-SGN, are with a sliding window, say SL, less than a segment length, say L1, of the overlapping segments, SG1-SGN, to allow overlapping of any successive two (such as SG1 and SG2; SG2 and SG3; and so on) of the overlapping segments. In some embodiment, the sliding window SL may be set to: $L1/2<SL<L1$; or $0<SL<L1/2$; or $SL=L1/2$. In other embodiments, the segment length may be set to two times the length L of a sequence read (denoted by R1 in FIG. 5), from the sequencing machine 2, for example; but the invention is not limited thereto, the segment length may be set arbitrarily for a suitable length.

In an example of the method shown in FIG. 6, the global database table has a NoSQL database format, such a generalized suffix-based big table, such as Apache HBase, HyperTable, MapR-DB, and so on. In an example of the method shown in FIG. 6, the step of generating the plurality of distributed database tables is based on common prefixes and corresponding remaining suffixes of the sorted expansion segments by the slave computing units. For instance, in the step of generating the plurality of distributed database tables, one of the distributed database tables has one node which includes: a first value based on a hash function of one of the common prefixes; a second value of the corresponding remaining suffix of the one of the common prefixes; and a link value associated with another node. In addition, the link value may be associated with another node of the distributed database tables, which is in another of the slave computer units or in the same one of the slave computer units.

Figure 7:
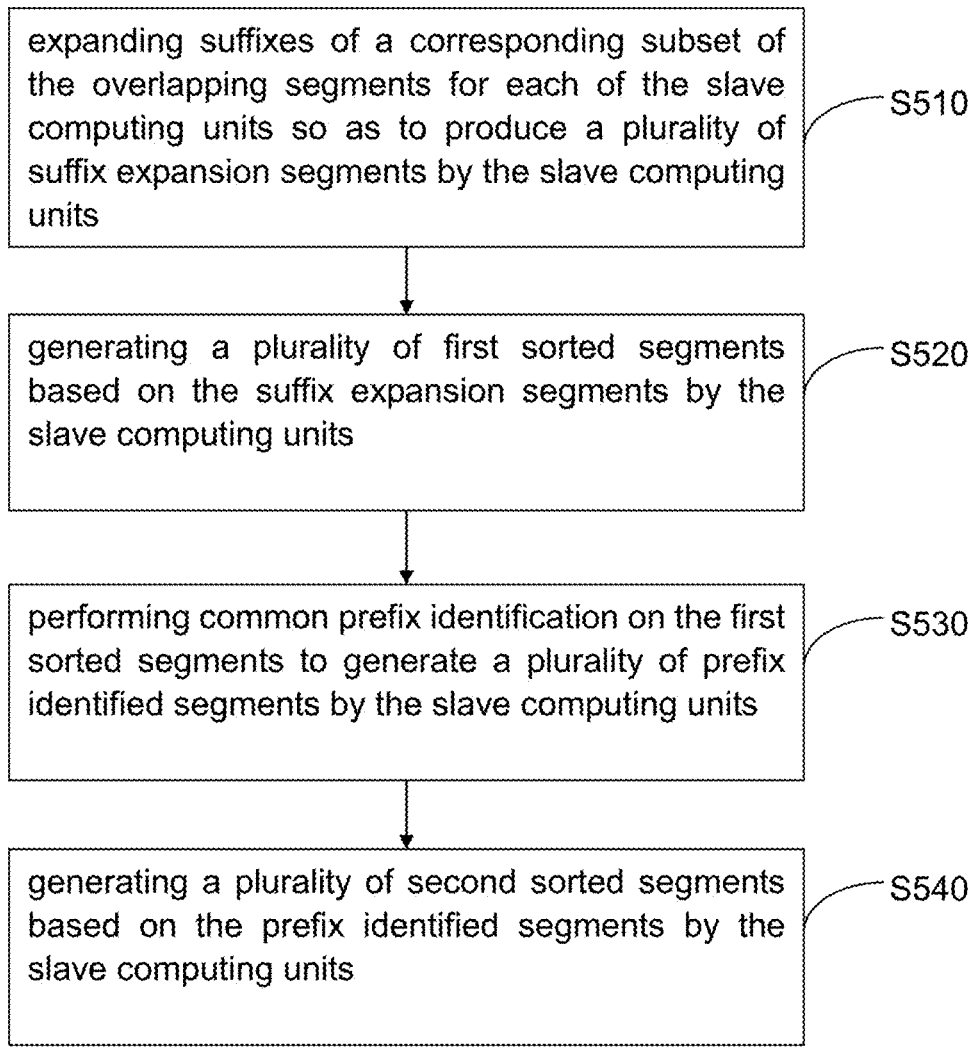
FIG. 7 is a flowchart showing the suffix-expansion-sorting processing of step S440 in FIG. 6, according to an embodiment.

FIG. 7 is a flowchart showing the suffix-expansion-sorting processing of step S440 in FIG. 6, according to an embodiment. As shown in FIG. 7, the suffix-expansion-sorting processing may comprise the following. In step S510, suffixes of a corresponding subset of the overlapping segments are expanded for each of the slave computing units so as to produce a plurality of suffix expansion segments by the slave computing units. In step S520, a plurality of first sorted segments are generated based on the suffix expansion segments by the slave computing units. For example, aggregation and/or sorting can be performed in step S520. In step S530, common prefix identification is performed on the first sorted segments to generate a plurality of prefix identified segments by the slave computing units. In step S540, a plurality of second sorted segments is generated based on the prefix identified segments by the slave computing units. The sorted expansion segments are based on the second sorted segments.

Figure 8:
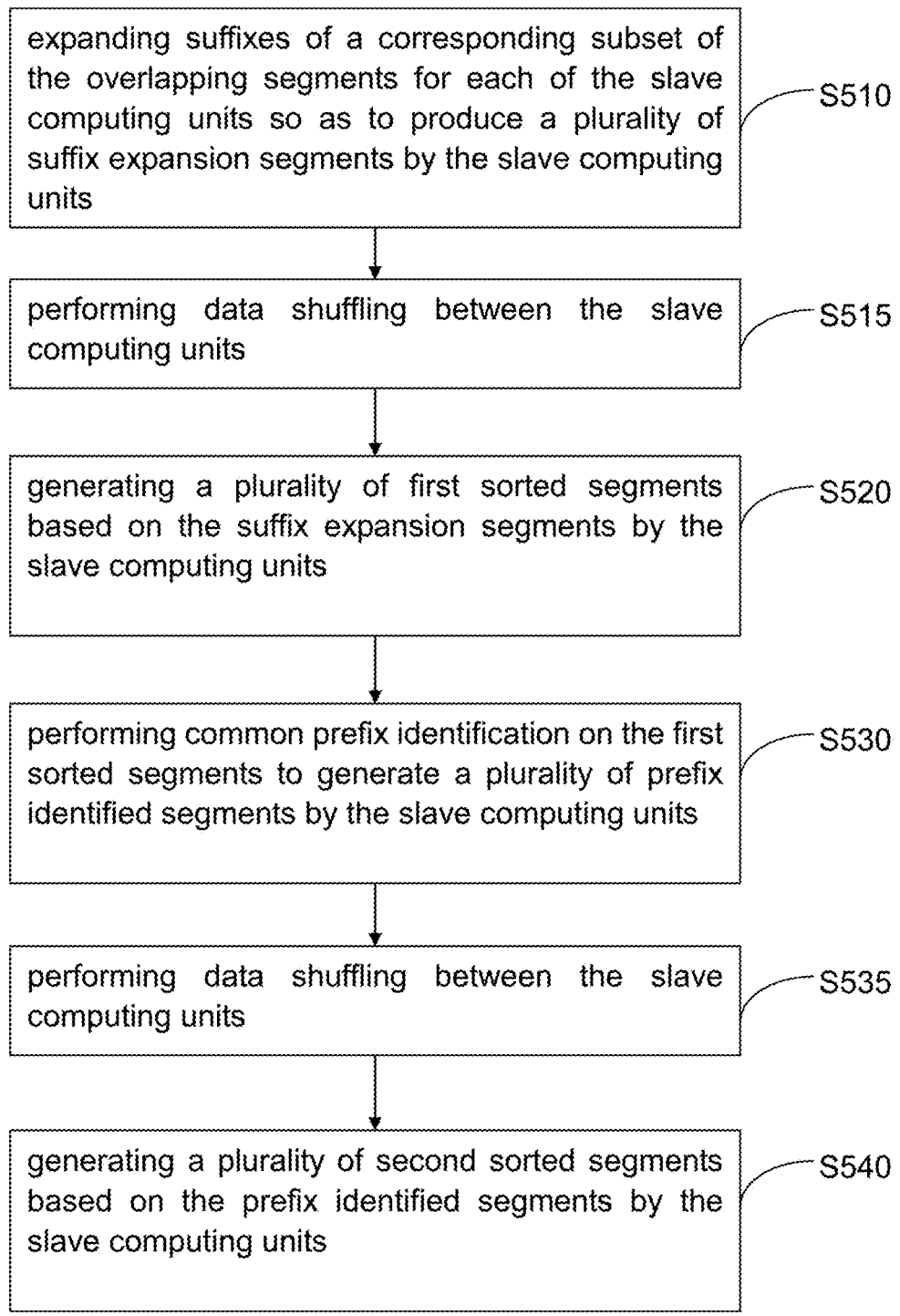
FIG. 8 is a flowchart showing the suffix-expansion-sorting processing of step S440 in FIG. 6, according to another embodiment.

FIG. 8 is a flowchart showing the suffix-expansion-sorting processing of step S440 in FIG. 6, according to another embodiment. In this embodiment, the suffix-expansion-sorting processing, as shown in FIG. 7, may further include performing data shuffling between the slave computing units, as indicated in step S515 and S535, optionally. In addition, the plurality of first sorted segments are generated based on the suffix expansion segments by the slave computing units after step S515. The plurality of second sorted segments are generated based on the prefix identified segments by the slave computing units after step S535. In other embodiment, data shuffling between the slave computing units may be utilized once only, i.e., as indicated by step S515 or S535. In these embodiments, data shuffling between the slave computing units is performed to enhance the performance of sorting among the slave computing units.

As mentioned above, data shuffling between the slave computing units can be implemented based on any distributed processing model for large-scale data-intensive applications, such as "MapReduce." The MapReduce programming model was proposed by Google to support data-intensive applications running on parallel computers like commodity clusters.

Specifically, two functional programming primitives in MapReduce are Map and Reduce. The Map function is applied on application specific input data to generate a list of intermediate <key, value> pairs. Then, the Reduce function is applied to the set of intermediate pairs with the same key. Typically, the Reduce function produces zero or more output pairs by performing a merging operation. All the output pairs are finally sorted based on their key values. Programmers only need to implement the Map and Reduce functions, because a MapReduce programming framework can facilitate some operations (e.g., grouping and sorting) on a set of <key, value> pairs.

For example, "Hadoop" is an implementation of the MapReduce model. The Hadoop framework has two main components: the MapReduce language and the Hadoop's Distributed File System (or HDFS for short). The Hadoop runtime system coupled with HDFS manages the details of parallelism and concurrency to provide ease of parallel programming with reinforced reliability. In a Hadoop cluster, a master node (e.g., which can be implemented on the computing unit 110) controls a group of slave nodes (e.g., which are implemented by the computing units 120) on which the Map and Reduce functions run in parallel. The master node assigns a task to a slave node that has any empty task slot. For example, computing nodes and storage nodes in a Hadoop cluster may be identical from the hardware's perspective. In other words, the Hadoop's Map/Reduce framework and the Hadoop's HDFS are, in many cases, running on a set of homogeneous nodes including both computing and storage nodes. Such a homogeneous configuration of Hadoop allows the Map/Reduce framework to effectively schedule computing tasks on an array of storage nodes where data files are residing, leading to a high aggregate bandwidth across the entire Hadoop cluster.

In addition, an input file passed to Map functions resides on the Hadoop distributed file system on a cluster. Hadoop's HDFS, which aims to provide high throughput access to large application data sets, splits the input file into even-sized fragments, which are distributed to a pool of slaves for further MapReduce processing.

However, the invention is not limited to any implementation of any distributed processing model for large-scale data-intensive applications, such as "MapReduce," as exemplified above. Any distributed processing model that facilitates the sorting across a plurality of slave computing units can be employed to implement the data shuffling recited in various embodiments of the invention. In other embodiments, the slave computing units may perform respective sorting tasks without communication therebetween, i.e., without the data shuffling.

In addition, the method of the embodiment in FIG. 6 is not limited to that as in FIG. 7 or 8; other modification can be utilized to implement the method of the FIG. 6. For example, in the suffix-expansion-sorting processing, as shown in FIG. 7 or 8, steps S510 and S520 may be replaced by other implementation; or steps S530 and S540 may be replaced by other implementation.

In an embodiment of the method in FIG. 6, 7, or 8, the distributed database tables are generated based on the sorted expansion segments by the slave computing units respectively. In this way, all of the slave computing units have respective distributed database tables which are to generate the global database table.

Figure 9:
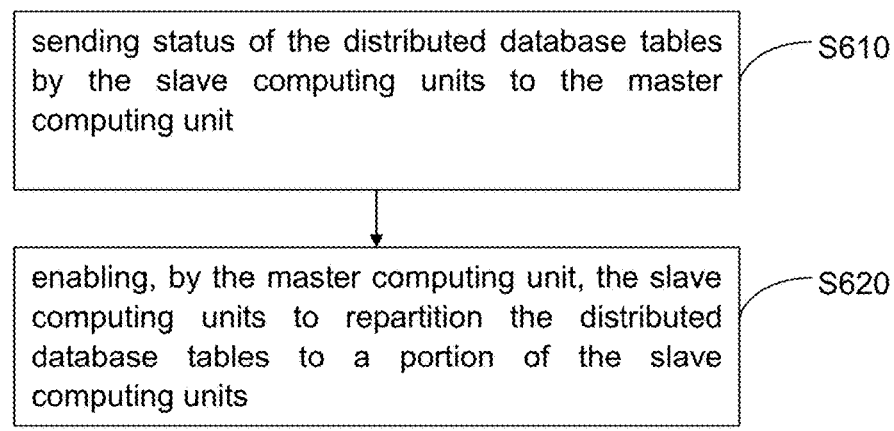
FIG. 9 is a flowchart showing further steps for the method for high-throughput sequencing data analysis, related to construction of a global database table, according to an embodiment.

In another embodiment of the method in FIG. 6, 7, or 8, the distributed database tables based on the sorted expansion segments are generated or stored by a portion of the slave computing units respectively. In this way, data load balancing with respect to the global database table can be achieved in which only some of the slave computing units are required to generate or store respective distributed database tables which are associated for the global database table. For example, FIG. 9 is a flowchart showing further steps for the method for high-throughput sequencing data analysis, related to construction of a global database table, according to an embodiment. As shown in FIG. 9, any embodiment of the method in FIG. 6, 7, or 8 may further include the following. In step S610, status of the distributed database tables is sent by the slave computing units to the master computing unit. For instance, the status of one of the distributed database table may be a hash value of that table. In step S620, the slave computing units are enabled by the master computing unit to reparation the distributed database tables to a portion of the slave computing units. For instance, only 25 of 100 slave computing units are required to store the distributed database tables, wherein the 100 slave computing units have been employed for facilitating processing, such as suffix processing and/or sorting processing, thus enhancing the speed of processing. In this way, computing resource of the slave computing units which are not included in the portion of the slave computing units can be released. In other embodiments, if data load balancing with respect to the global database table is not performed, e.g., by the steps exemplified in FIG. 9, all the slave computing units are required to generate and/or store the distributed database table. However, the invention is not limited thereto; other approach for data load balancing can also be done optionally.

Figure 10:
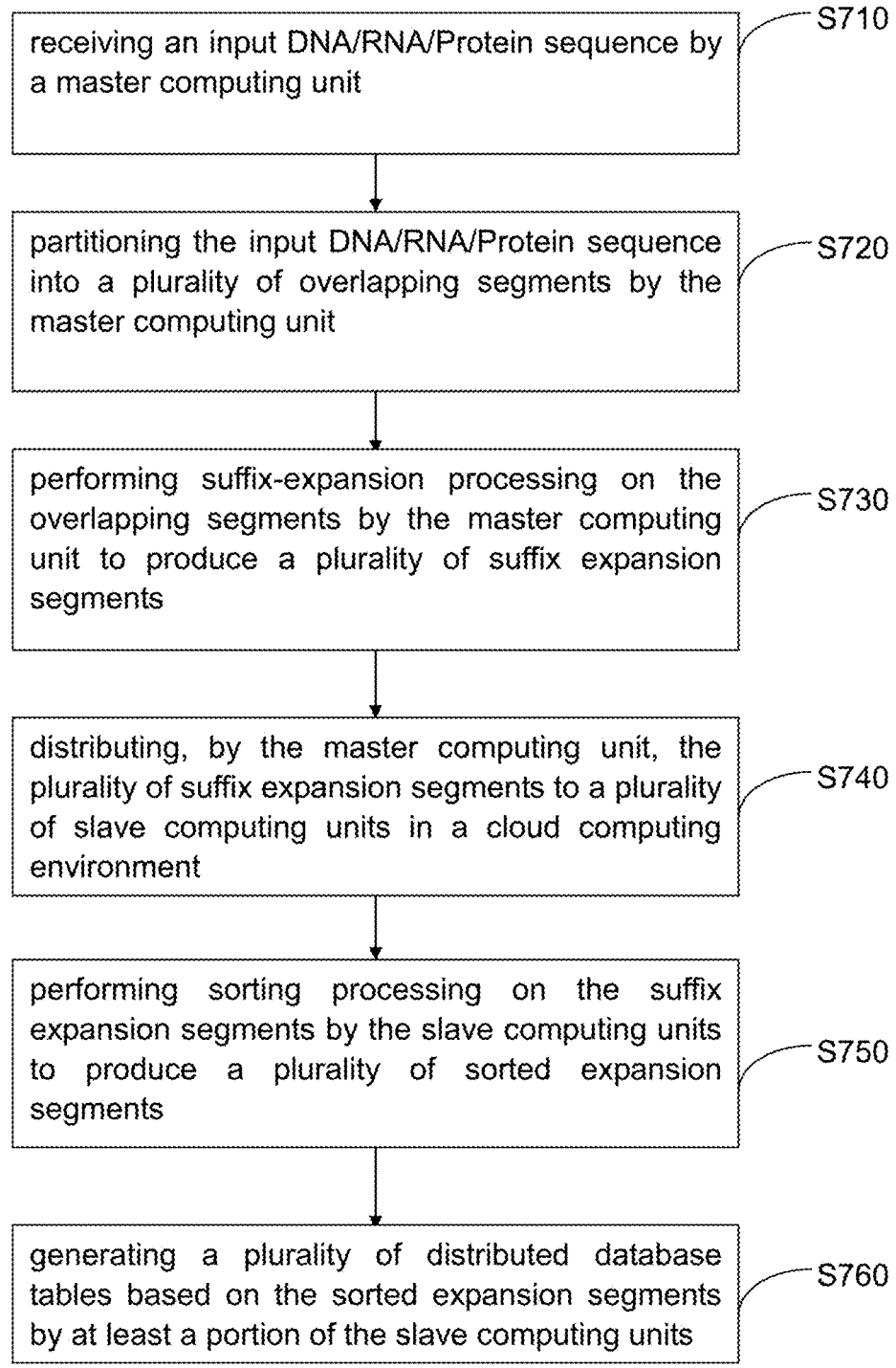
FIG. 10 is a flowchart showing a method for high-throughput sequencing data analysis, related to construction of a global database table, according to an embodiment.

FIG. 10 is a flowchart showing a method for high-throughput sequencing data analysis, related to construction of a global database table, according to another embodiment. In contrast to the embodiment of FIG. 6, the master computing unit in this embodiment further performs suffix-expansion processing before distributing the partitioned segments. In this way, the slave computing units in this embodiment may perform reduced processing for the construction of the global database table. In addition, any example or embodiment of the method in FIG. 6, 7, 8 or 9 may be applied to the embodiment of the method in FIG. 10 if appropriate.

As shown in FIG. 10, the method for high-throughput sequencing data analysis includes the following. In step S710, an input DNA/RNA/Protein sequence is received by a master computing unit, such as the computing unit 110 as illustrated in FIG. 1. In step S720, the input DNA/RNA/Protein sequence is partitioned into a plurality of overlapping segments with a sliding window less than a segment length of the overlapping segments to allow overlapping of any successive two of the overlapping segments by the master computing unit, as exemplified in any example or embodiment of step S430 or FIG. 5 above. In step S730, suffix-expansion processing is performed on the overlapping segments by the master computing unit to produce a plurality of suffix expansion segments. In step S740, the plurality of suffix expansion segments are distributed, by the master computing unit, to a plurality of slave computing units, such as the computing units 120 as illustrated in FIG. 1, in a cloud computing environment. In step S750, sorting processing is performed on the suffix expansion segments by the slave computing units to produce a plurality of sorted expansion segments. In step S760, a plurality of distributed database tables are generated based on the sorted expansion segments by at least a portion of the slave computing units, as exemplified in any example or embodiment of step S450 above. The distributed database tables generated by the slave computing units are associated to construct a global database table corresponding to the input DNA/RNA/Protein sequence for high-throughput sequencing data analysis.

Figure 11:
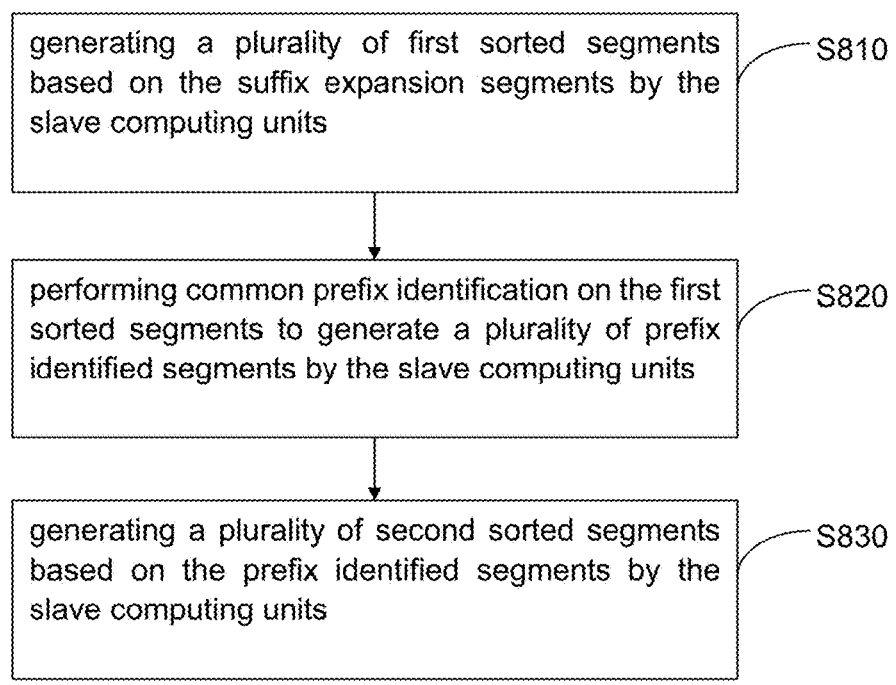
FIG. 11 is a flowchart showing the sorting processing of step S750 in FIG. 10, according to an embodiment.

FIG. 11 is a flowchart showing the sorting processing of step S750 in FIG. 10, according to an embodiment. As shown in FIG. 11, the sorting processing of step S750 may comprises the following. In step S810, a plurality of first sorted segments are generated based on the suffix expansion segments by the slave computing units. In step S820, common prefix identification is performed on the first sorted segments to generate a plurality of prefix identified segments by the slave computing units. In step S830, a plurality of second sorted segments are generated based on the prefix identified segments by the slave computing units. The sorted expansion segments are based on the second sorted segments.

In other embodiments of the sorting processing of step S750 in FIG. 10, the sorting processing, as shown in FIG. 11, may further include performing data shuffling between the slave computing units, as indicated in step S515 and/or S535 in FIG. 8, optionally. In one example, step S810 is performed after data shuffling; or data shuffling is performed before step S810. In another example, step S830 is performed after data shuffling; or data shuffling is performed before step S830. In other embodiment, data shuffling between the slave computing units may be utilized once, twice or above.

In addition, the method of the embodiment in FIG. 10 is not limited to that as in FIG. 11 or 8; other modification can be utilized to implement the method of the FIG. 10. For example, in the sorting processing, as shown in FIG. 11, steps S810 may be replaced by other implementation; or steps S820 and S830 may be replaced by other implementation.

In an embodiment of the method in FIG. 10 or 11, the distributed database tables are generated based on the sorted expansion segments by the slave computing units respectively. In this way, all of the slave computing units have respective distributed database tables which are to generate the global database table.

In another embodiment of the method in FIG. 10 or 11, the distributed database tables are generated based on the sorted expansion segments by a portion of the slave computing units respectively. In this way, only some of the slave computing units have respective distributed database tables which are to generate the global database table so that the global database table load balancing can be achieved. For example, FIG. 9 is a flowchart showing further steps for the method for high-throughput sequencing data analysis, related to construction of a global database table, according to an embodiment. In this way, computing resource of the slave computing units which are not included in the portion of the slave computing units can be released.

In the following, examples for construction of a tree according to segments of a DNA sequence are provided.

Suffix Expansion

In an example as illustrated in Table 1, the two segments of a DNA sequence, say "ATCGAATTCCGG" (SEQ ID NO: 1) and "GCTAAATTCCGG," (SEQ ID NO: 2) are provided, and suffix expansion is performed on the segments, wherein values are assigned to the suffixes as well as the segments for indexing purpose. In addition, the exemplary segments of DNA sequence in Table 1 are fictitious and are provided to illustrate the methods of the embodiments according to the invention.

TABLE 1

| Segment | Value | Suffix Expansion | Value |
|---|---|---|---|
| ATCGAATTCCGG (SEQ ID NO: 1) | 100 | ATCGAATTCCGG (SEQ ID NO: 1) | 100 |
| | | TCGAATTCCGG (SEQ ID NO: 3) | 101 |
| | | CGAATTCCGG (SEQ ID NO: 4) | 102 |
| | | GAATTCCGG | 103 |
| | | AATTCCGG | 104 |
| | | ATTCCGG | 105 |
| | | TTCCGG | 106 |
| | | TCCGG | 107 |
| | | CCGG | 108 |
| | | CGG | 109 |
| | | GG | 110 |
| | | G | 111 |
| GCTAAATTCCGG (SEQ ID NO: 2) | 500 | GCTAAATTCCGG (SEQ ID NO: 2) | 500 |
| | | CTAAATTCCGG (SEQ ID NO: 5) | 501 |
| | | TAAATTCCGG (SEQ ID NO: 6) | 502 |
| | | AAATTCCGG | 503 |
| | | AATTCCGG | 504 |
| | | ATTCCGG | 505 |
| | | TTCCGG | 506 |
| | | TCCGG | 507 |
| | | CCGG | 508 |
| | | CGG | 509 |
| | | GG | 510 |
| | | G | 511 |

Aggregation & Sorting

In an example, sorting, or aggregation and sorting, can be performed on the suffixes generated by way of the suffix expansion, as illustrated in Table 2 below, to generate a plurality of sorted expansion segments.

TABLE 2

| Aggregation & Sorting | Value |
|---|---|
| AAATTCCGG | 503 |
| AATTCCGG | 104, 504 |

TABLE 2-continued

| Aggregation & Sorting | Value |
|---|---|
| ATCGAATTCCGG | 100 |
| ATTCCGG | 105, 505 |
| CCGG | 108, 508 |
| CGAATTCCGG | 102 |
| CGG | 109, 509 |
| CTAAATTCCGG | 501 |
| G | 111, 511 |
| GAATTCCGG | 103 |
| GCTAAATTCCGG | 500 |
| GG | 110, 510 |
| TAAATTCCGG | 502 |
| TCCGG | 107, 507 |
| TCGAATTCCGG | 101 |
| TTCCGG | 106, 506 |

Common Prefix Identification

In this example, common prefix of the sorted expansion segments can be further identified, e.g., by way of comparing two adjacent segments, as illustrated in Table 3, wherein a token may be inserted or indicated otherwise for further processing. For the sake of illustration only, a common sign is inserted in the segments after the identification, wherein some segments have the common code before the common sign. For a segment that there are no other segments with the same common prefix, the token is placed in the beginning. However, the common prefix identification is not limited thereto; any way of indication of the common prefix of the segments can be employed, such as an index number indicating the number of characters of the prefix can be employed, rather than the token as illustrated above.

TABLE 3

| Common Prefix Identification | Value |
|---|---|
| ,AAATTCCGG | 503 |
| AA,ATTCCGG | 503 |
| AA,TTCCGG | 104, 504 |
| A,ATTCCGG | 104, 504 |
| A,TCGAATTCCGG | 100 |
| AT,CGAATTCCGG | 100 |
| AT,TCCGG | 105, 505 |
| ,ATTCCGG | 105, 505 |
| ,CCGG | 108, 508 |
| C,CGG | 108, 508 |
| C,GAATTCCGG | 102 |
| CG,AATTCCGG | 102 |
| CG,G | 109, 509 |
| C,GG | 109, 509 |
| C,TAAATTCCGG | 501 |
| ,CTAAATTCCGG | 501 |
| ,G | 111, 511 |
| G, | 111, 511 |
| G,AATTCCGG | 103 |
| G,AATTCCGG | 103 |
| G,CTAAATTCCGG | 500 |
| G,CTAAATTCCGG | 500 |
| G,G | 110, 510 |
| ,GG | 110, 510 |
| ,TAAATTCCGG | 502 |
| T,AAATTCCGG | 502 |
| T,CCGG | 107, 507 |
| TC,CGG | 107, 507 |
| TC,GAATTCCGG | 101 |
| T,CGAATTCCGG | 101 |
| T,TCCGG | 106, 506 |
| ,TTCCGG | 106, 506 |

Sorting

In this sorting processing, sorting is performed on the segments obtained after the common prefix identification, as illustrated in Table 4 below.

TABLE 4

| Aggregation & Sorting | Value |
|---|---|
| ,AAATTCCGG | 503 |
| ,ATTCCGG | 105, 505 |
| ,CCGG | 108, 508 |
| ,CTAAATTCCGG | 501 |
| ,G | 111, 511 |
| ,GG | 110, 510 |
| ,TAAATTCCGG | 502 |
| ,TTCCGG | 106, 506 |
| A,ATTCCGG | 104, 504 |
| A,TCGAATTCCGG | 100 |
| AA,ATTCCGG | 503 |
| AA,TTCCGG | 104, 504 |
| AT,CGAATTCCGG | 100 |
| AT,TCCGG | 105, 505 |
| C,CGG | 108, 508 |
| C,GAATTCCGG | 102 |
| C,GG | 109, 509 |
| C,TAAATTCCGG | 501 |
| CG,AATTCCGG | 102 |
| CG,G | 109, 509 |
| G, | 111, 511 |
| G,AATTCCGG | 103 |
| G,AATTCCGG | 103 |
| G,CTAAATTCCGG | 500 |
| G,CTAAATTCCGG | 500 |
| G,G | 110, 510 |
| T,AAATTCCGG | 502 |
| T,CCGG | 107, 507 |
| T,CGAATTCCGG | 101 |
| T,TCCGG | 106, 506 |
| TC,CGG | 107, 507 |
| TC,GAATTCCGG | 101 |

Rowkey Generation and Bigtable Construction

In this example, a tree (data structure) for the segments of the DNA sequence can be constructed. The tree can be in terms of a global database table, e.g., a Bigtable, which are constructed by the association of the distributed database tables mentioned in various embodiments of the method as illustrated in FIGS. 2-4, 6-11. The distributed database table in this example has nodes (data structure) based on the format of Bigtable, each of which includes a "rowkey"

Figure 12:
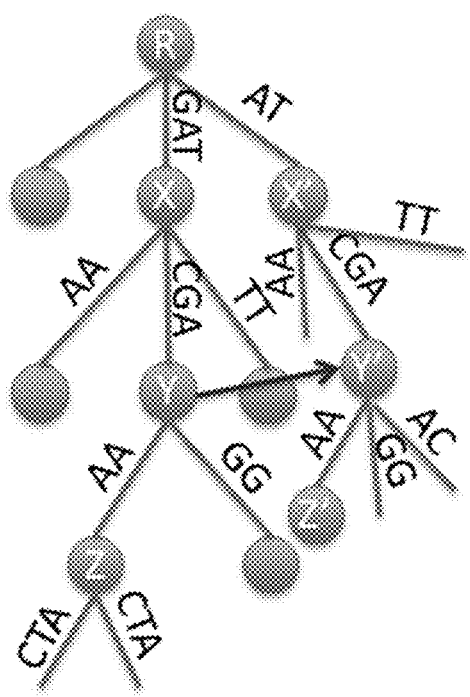
FIG. 12 is a schematic diagram illustrating a tree data structure in terms of nodes for a DNA sequence.

For the sake of illustration, the rowkeys of nodes are generated as shown in Table 5, and the tree representation of the nodes can be illustrated in FIG. 12.

TABLE 5

| Rowkey | next | Aggregation & Sorting | Value |
|---|---|---|---|
| . (i.e., root) | A, | ,AAATTCCGG | 503 |
| | C, | ,ATTCCGG | 105, 505 |
| | G | ,CCGG | 108, 508 |
| | | ,CTAAATTCCGG | 501 |
| | | ,G | 111, 511 |
| | | ,GG | 110, 510 |
| | | ,TAAATTCCGG | 502 |
| | | ,TTCCGG | 106, 506 |
| A | A, | A,ATTCCGG | 104, 504 |
| | T | A,TCGAATTCCGG | 100 |
| AA | A, | AA,ATTCCGG | 503 |
| | T | AA,TTCCGG | 104, 504 |
| AT | C, | AT,CGAATTCCGG | 100 |
| | T | AT,TCCGG | 105, 505 |
| C | C, | C,CGG | 108, 508 |
| | G, | C,GAATTCCGG | 102 |
| | T | C,GG | 109, 509 |
| | | C,TAAATTCCGG | 501 |
| CG | A, | CG,AATTCCGG | 102 |
| | G | CG,G | 109, 509 |
| G | A, | G, | 111, 511 |
| | C, | G,AATTCCGG | 103 |
| | G | G,AATTCCGG | 103 |
| | | G,CTAAATTCCGG | 500 |
| | | G,CTAAATTCCGG | 500 |
| | | G,G | 110, 510 |
| T | A, | T,AAATTCCGG | 502 |
| | C, | T,CCGG | 107, 507 |
| | T | T,CGAATTCCGG | 101 |
| | | T,TCCGG | 106, 506 |
| TC | C, | TC,CGG | 107, 507 |
| | G | TC,GAATTCCGG | 101 |

BigTable

In this example, a distributed database table in a slave computing unit has each node which includes: a first value, a second value, and a link value. The first value, e.g., a rowkey, is based on a hash function (e.g., MD5) of one of the common prefixes. The second value is the corresponding remaining suffix of the one of the common prefixes. The link value, e.g., a suffix link, is associated with another node, which may be in the distributed database table in the same or another computing unit (e.g., slave computing unit). An example is taken as illustrated in Table 6. In addition, the global database table (e.g., Bigtable) includes the distributed database tables in the slave computing units, wherein a root tablet can be employed or comprised to include the locations and/or metadata pointed to the location of the distributed database tables in the slave computing units (e.g, as in the BigTable system).

TABLE 6

| Node | Rowkey | Column | Value |
|---|---|---|---|
| X | MD5(Root) + G | R2P | null |
| | | P2S | GAT |
| | | Next | A, C, T |
| | | Suffix Link | MD5(Root) |
| Y | MD5(GAT) + C | R2P | GAT |
| | | P2S | CGA |
| | | Next | A, G |
| | | Suffix Link | MD5(AT) + C |

TABLE 6-continued

| Node | Rowkey | Column | Value |
|---|---|---|---|
| Z | MD5(GATCGA) + A | R2P | GATCGA |
| | | P2S | AA |
| | | Next | A, C |
| | | Suffix Link | MD5(ATCGA) + A |

Computing Units in a Cloud Environment

Figure 13:
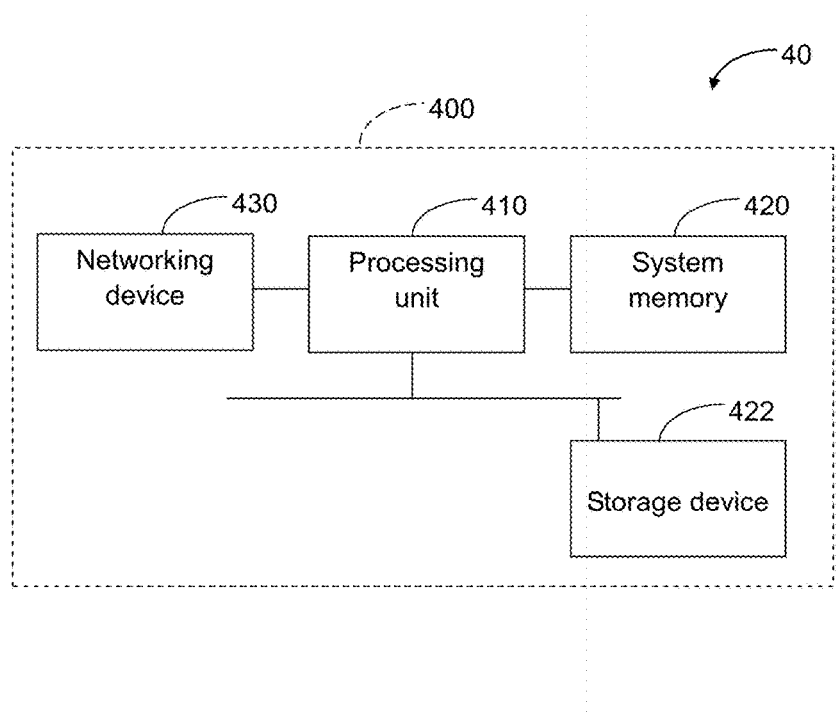
FIG. 13 is a block diagram showing a computing node, according to various embodiments.

In addition, the master computing unit 10 and the slave computing units 20 each can be implemented as computing nodes, in a network or in a cloud computing environment. Referring now to FIG. 13, a schematic of an example of a computing node 40 is shown. The computing node 40 is only one example of a suitable computing node and is not intended to suggest any limitation as to the scope of use or functionality of embodiments of the invention described herein. Regardless, the computing node 40 is capable of being implemented and/or performing any of the functionality set forth hereinabove for the master computing unit 10 or the slave computing units 20.

In the computing node 40, there is a computer system 400 which may include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system 400 may be described in the general context of computer system-executable instructions, such as program modules, being executed by a computer system. The computer system 400 may be practiced in distributed cloud computing environments where tasks are performed by remote processing devices that are linked via one or more communications network (such as internet, mobile communication network, and so on). In a distributed cloud computing environment, program modules may be located in both local and remote computer system storage media including memory storage devices.

As shown in FIG. 13, the computer system 400 in the computing node 40 is shown in the form of a general-purpose computing device. The components of the computer system 400 may include, but are not limited to, one or more processors or processing units 410, a system memory 420, and a networking device 430; and one or more buses is provided to couple various system components including the system memory 420 to the processing unit 410, the system memory 420, and the networking device 430. In addition, the first access control unit can also be implemented based on the structure as illustrated in FIG. 8, but the invention is not limited thereto.

The system memory 420 can include computer system readable media in the form of volatile memory, such as random access memory (RAM) and/or cache memory. The computer system 400 may further include other removable/non-removable, volatile/non-volatile computer system storage media. As will be further depicted and described below, the system memory 420 may include at least one program product having a set (e.g., at least one) of program modules that are configured to carry out the functions of embodiments according to the invention. In addition, one or more storage devices 422 may be included in the computer system 400.

The networking device 430 can be configured by the processing unit 410 to communicate with another computer node, such as another slave computing unit 120 and/or the master computing unit 110.

II. Searching of Sequence Pattern.

In addition to the embodiments of construction of a global database table as exemplified above, embodiments of searching of sequence patterns are provided.

Figure 14:
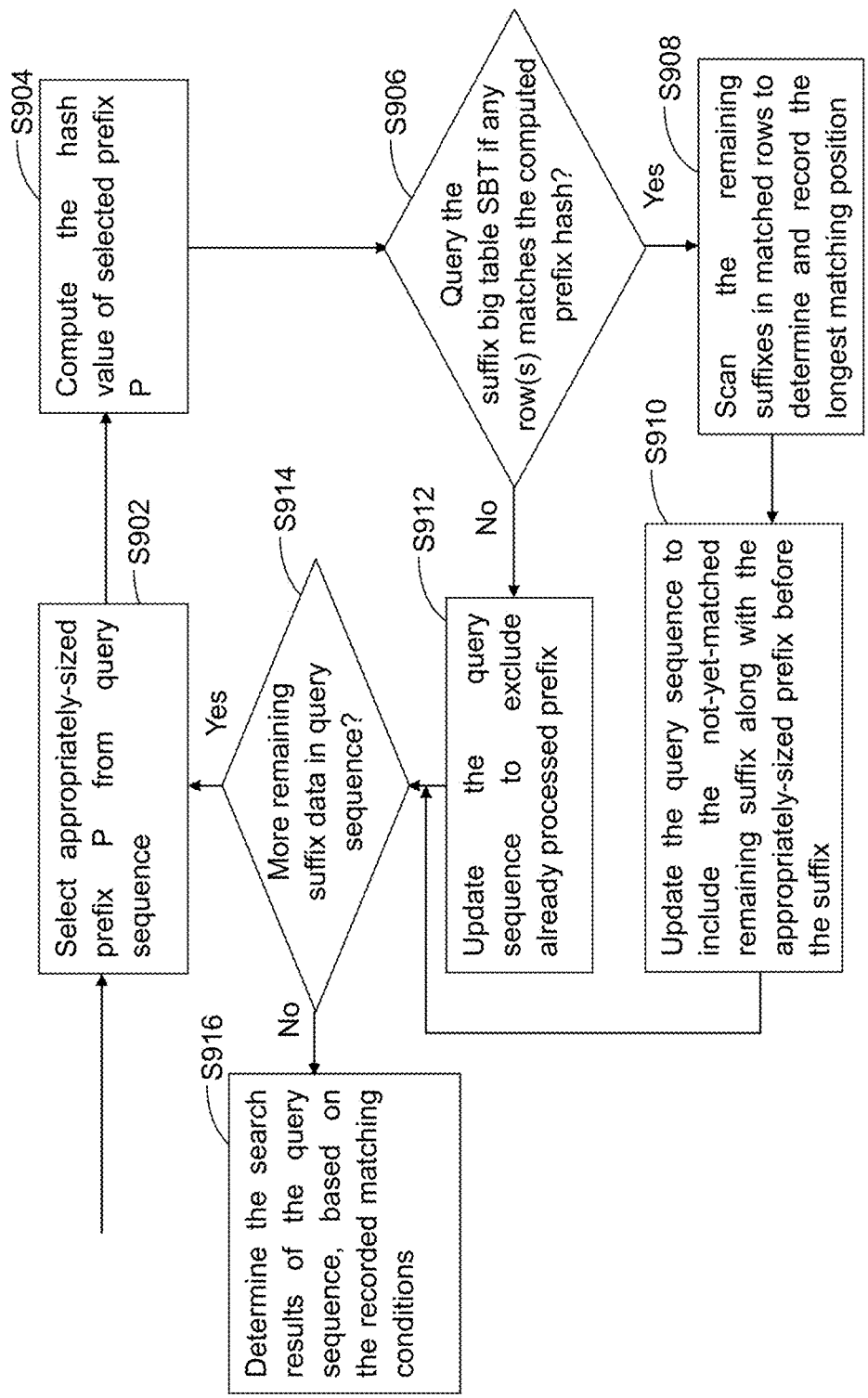
FIG. 14 is a flowchart showing searching of sequence pattern in a global database table, according to an embodiment.

FIG. 14 is a flowchart showing searching of sequence pattern in a global database table, according to an embodiment. For example, as shown in FIG. 13, an appropriately-sized prefix P is selected from query sequence, as in step S902. In step S904, the hash value of the selected prefix P is computed. In step S906, the suffix big table SBT is queried as to determine whether any row(s) matches the computed prefix hash. If so, the remaining suffixes in matched rows are scanned to determine and record the longest matching position, as in step S908. After that, the query sequence is updated to include the not-yet-matched remaining suffix along with the appropriately-sized prefix before the suffix, as in step S910. Afterwards, the method proceeds to step S914. If it is determined that no row matches the computed prefix hash, the query sequence is then updated to exclude already processed prefix, as indicated in step S912. In step S914, it is determined whether more remaining suffix data is in query sequence. If so, the method proceeds to step S902 for the next prefix. If not, the search results of the query sequence are determined, based on the recorded matching conditions, as indicated in step S916.

III. Exploratory Data Mining by Cluster Analysis.

Furthermore, embodiments of exploratory data mining by cluster analysis are provided.

In an embodiment, clustering is the classification of objects into different groups, or more precisely, the partitioning of an object set into subsets (clusters), so that the objects in each subset share some common trait or feature. In some embodiments of this invention, the "objects" are represented by sequences whilst the "common trait/feature" is the union of the common longest possible segments of sequences in the same cluster, which can be visualized in a form of graphical user interface.

In an embodiment, after the construction of the global database table (such as suffix-based big table (SBT), based on the recorded object information in table rows the methodology proceeds by the following 3-step process:

(a) Identify all object clusters by scanning the SBT table rows, each of which represents a single candidate cluster where all object(s) share the same single sequence segment. Each candidate cluster is filtered by a scoring function that eliminates any cluster with score lower than a predefined threshold. Two variables, the number of objects and the length of the common segment, along with a weighting factor that penalizes shorter common segment, can define the scoring function of a given cluster.

(b) From the cluster candidates outputted in above step, remove the clusters which common prefix is itself the prefix or portion of the common prefix of other clusters. This is to eliminate clusters with features that are too common in the object population.

(c) Lastly the cluster candidates are merged to form the maximal clusters by a set operation upon the object sets of two given cluster candidates. The set operation is performed with a factor scale between 0 and 1. The Merge factor is used to apply on and merge those clusters with a certain level of overlapping among their object sets, i.e. the higher the merge factor is, the higher the overlapping of two object sets is required. By given two object sets, if the set ratio of the two object sets is greater than or equal to the merge factor, than we merge the two clusters to form a new maximal cluster. The Drop factor is used to drop those insignificantly small clusters, which object set has relatively small overlapping with other clusters.

IV. Common Sequence Visualization

After building the aforementioned global database table (e.g., bigtable) of sequences, the groups of sequence objects can be further identified. Each of the group includes all objects includes the same one or more sequence segments.

Figure 15:
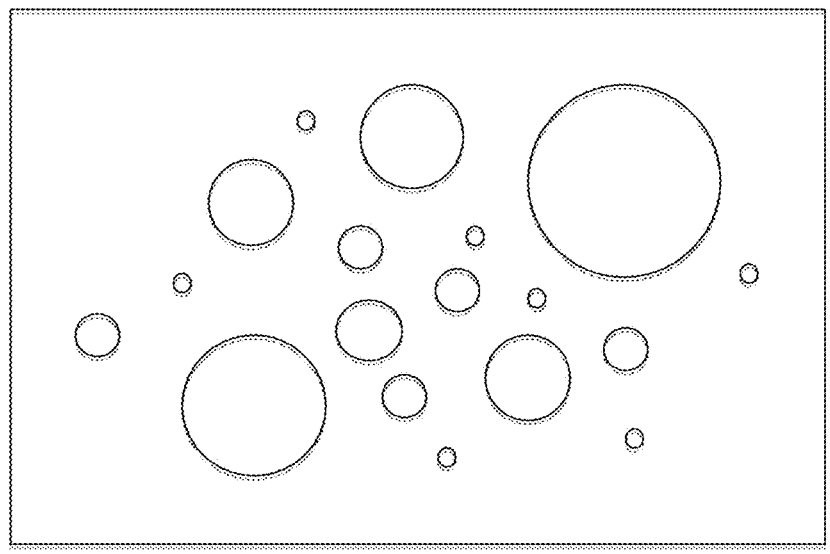
FIGS. 15 and 16 are schematic diagrams illustrating examples of representation of searching results, according to various embodiments.

FIGS. 14 and 15 are schematic diagrams illustrating examples of representation of searching results, according to various embodiments.

In FIG. 15, each group is represented by a closing shape, e.g., circle, rectangle, or alike. The size of the shape is determined by the number of objects and the number of common sequence segments within the group. Each shape can be clicked to show more details of the group, as exemplified in FIG. 16.

Figure 16:
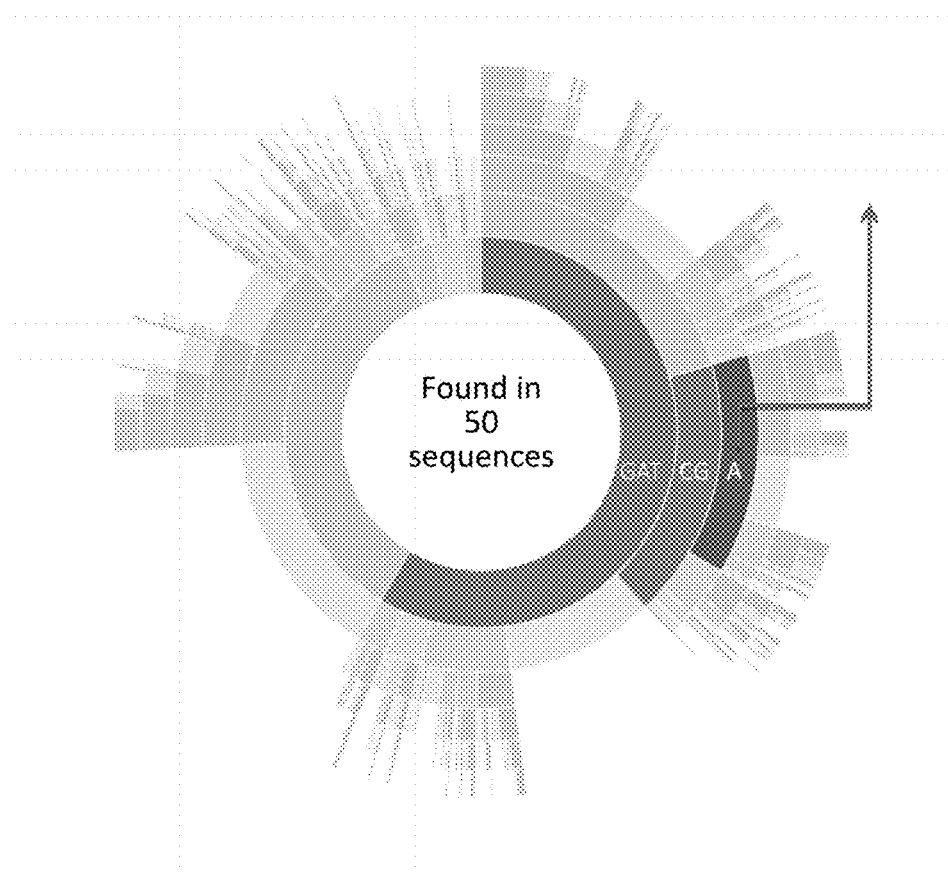

In FIG. 16, the details of a group can be represented by a sunburst-like chart. For example, an area indicated by A, when clicked, further information can be presented in a pop-up window or in other manner.

It will be apparent to those skilled in the art that various modifications and variations can be made to the present disclosure without departing from the spirit and scope of the disclosure. Thus it is intended that the present disclosure cover the modifications and variations of this disclosure provided they come within the scope of the appended claims and their equivalents.

What is claimed is:

1. A method for high-throughput sequencing data analysis, comprising:

receiving, by a master computing unit, a plurality of sequence reads generated from a Next-Generation Sequencer (NGS) or a third generation DNA sequencer;

partitioning, by the master computing unit, the plurality of sequence reads into a plurality of overlapping segments with a sliding window less than a segment length of the overlapping segments to allow overlapping of any successive two of the overlapping segments;

distributing, by the master computing unit, the plurality of overlapping segments to a plurality of slave computing units in a cloud computing environment;

performing suffix-expansion-sorting processing on the overlapping segments by the slave computing units to produce a plurality of sorted expansion segments; and generating a plurality of distributed database tables based on common prefixes and corresponding remaining suffixes of a plurality of the sorted expansion segments by the slave computing units;

wherein the suffix-expansion-sorting processing comprises:

expanding suffixes of a corresponding subset of the overlapping segments for each of the slave computing units so as to produce a plurality of suffix expansion segments by the slave computing units;

generating a plurality of first sorted segments based on the suffix expansion segments by the slave computing units, wherein the sorted expansion segments are based on the first sorted segments;

performing common prefix identification on the first sorted segments to generate a plurality of prefix identified segments by the slave computing units; and generating a plurality of second sorted segments based on the prefix identified segments by the slave computing units, wherein the sorted expansion segments are based on the second sorted segments; and wherein the distributed database tables are associated to construct a global database table corresponding to the plurality of sequence reads for high-throughput sequencing data analysis.

2. The method according to claim 1, wherein the global database table has a NoSQL database format.

3. The method according to claim 1, wherein in the step of generating the plurality of distributed database tables, one of the distributed database tables has one node which includes:

a first value based on a hash function of one of the common prefixes;

a second value of the corresponding remaining suffix of the one of the common prefixes; and a link value associated with another node.

4. The method according to claim 3, wherein the link value is associated with another node of the distributed database tables, which is in another of the slave computer units or in the same one of the slave computer units.

5. The method according to claim 1, wherein the distributed database tables are generated based on the sorted expansion segments by the slave computing units respectively.

6. The method according to claim 1, wherein the method further comprising:

sending status of the distributed database tables by the slave computing units to the master computing unit; and enabling, by the master computing unit, the slave computing units to repartition the distributed database tables to a portion of the slave computing units.

7. A method for high-throughput sequencing data analysis, comprising:

receiving, by a master computing unit, a plurality of sequence reads generated from a Next-Generation Sequencer (NGS) or a third generation DNA sequencer;

partitioning, by the master computing unit, the plurality of sequence reads into a plurality of overlapping segments with a sliding window less than a segment length of the overlapping segments to allow overlapping of any successive two of the overlapping segments;

performing suffix-expansion processing on the overlapping segments by the master computing unit to produce a plurality of suffix expansion segments;

distributing, by the master computing unit, the plurality of suffix expansion segments to a plurality of slave computing units in a cloud computing environment;

performing sorting processing on the suffix expansion segments by the slave computing units to produce a plurality of sorted expansion segments; and generating a plurality of distributed database tables based on common prefixes and corresponding remaining suffixes of a plurality of the sorted expansion segments by the slave computing units;

wherein the suffix-expansion processing comprises:

expanding suffixes of a corresponding subset of the overlapping segments for each of the slave computing units so as to produce a plurality of suffix expansion segments by the slave computing units;

wherein the sorting processing comprises:

generating a plurality of first sorted segments based on the suffix expansion segments by the slave computing units, wherein the sorted expansion segments are based on the first sorted segments;

performing data shuffling between the slave computing units, wherein the plurality of first sorted segments are generated based on the suffix expansion segments by the slave computing units after the step of performing data shuffling;

performing common prefix identification on the first sorted segments to generate a plurality of prefix identified segments by the slave computing units;

generating a plurality of second sorted segments based on the prefix identified segments by the slave computing units, wherein the sorted expansion segments are based on the second sorted segments; and performing data shuffling between the slave computing units, wherein the plurality of second sorted segments are generated based on the prefix identified segments by the slave computing units after the step of performing data shuffling; and wherein the distributed database tables are associated to construct a global database table corresponding to the plurality of sequence reads for high-throughput sequencing data analysis.

8. The method according to claim 7, wherein the global database table has a NoSQL database format.

9. The method according to claim 7, wherein in the step of generating the plurality of distributed database tables, one of the distributed database tables has one node which includes:

a first value based on a hash function of one of the common prefixes;

a second value of the corresponding remaining suffix of the one of the common prefixes; and a link value associated with another node.

10. The method according to claim 9, wherein the link value is associated with another node of the distributed database tables, which is in another of the slave computer units or in the same one of the slave computer units.

11. The method according to claim 7, wherein the distributed database tables are generated based on the sorted expansion segments by the slave computing units respectively.

12. The method according to claim 7, wherein the method further comprising:
- sending status of the distributed database tables by the slave computing units to the master computing unit; and
- enabling, by the master computing unit, the slave computing units to repartition the distributed database tables to a portion of the slave computing units.

* * * * *